(12) United States Patent
Garst et al.

(10) Patent No.: US 6,271,220 B1
(45) Date of Patent: Aug. 7, 2001

(54) ANTI-ANGIOGENIC AGENTS

(75) Inventors: Michael E. Garst, Newport Beach, CA (US); Timothy L. MacDonald, Charlottesville, VA (US)

(73) Assignee: Allergan Sales, Inc.

(*) Notice: Subject to any disclaimer, the term of this patent is extended or adjusted under 35 U.S.C. 154(b) by 0 days.

(21) Appl. No.: 09/380,866

(22) PCT Filed: Mar. 11, 1998

(86) PCT No.: PCT/US98/04711

§ 371 Date: Sep. 3, 1999

§ 102(e) Date: Sep. 3, 1999

(87) PCT Pub. No.: WO98/40077

PCT Pub. Date: Sep. 17, 1998

(51) Int. Cl.[7] .............................. A61K 31/56; C07J 1/00; C07J 5/00; C07J 7/00
(52) U.S. Cl. ........................ 514/177; 514/178; 514/179; 514/182; 552/558; 552/614; 552/617; 552/625; 552/627
(58) Field of Search .................................. 514/177, 178, 514/179, 182; 552/558, 614, 617, 625, 627

(56) References Cited

FOREIGN PATENT DOCUMENTS

WO 95/04535 * 2/1995 (US).

* cited by examiner

*Primary Examiner*—Joseph K. McKane
*Assistant Examiner*—Joseph Murray
(74) *Attorney, Agent, or Firm*—Robert J. Baran; Martin A. Voet; Carlos A. Fisher

(57) ABSTRACT

The application discloses methods of treating mammalian diseases characterized by undesirable angiogenesis by administering compounds including those having the general formulae

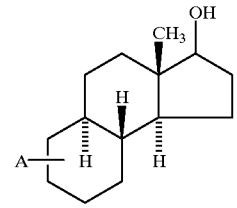

wherein A is a fused tropone having a general formula:

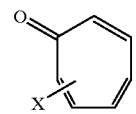

I

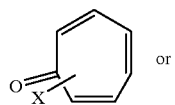

II or

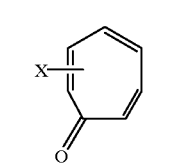

III wherein X is selected from the group consisting of hydrogen, hydroxy, carboxy, halogen, nitro, $C_1$ to $C_{12}$ alkenyl, $C_1$ to $C_{12}$ alkyl, $C_1$ to $C_{12}$ alkoxy, SR, $NR_2$, $OSO_3^-$, $OSO_2NR_2$, $HNSO_3^-$, $NHSO_2NR_2$, $SSO_3^-$, $SSO_2NR_2$, wherein R is hydrogen or a $C_1$ to $C_6$ alkyl and the 17-ester and keto derivatives thereof, in a dosage sufficient to inhibit cell mitosis. The application discloses novel compounds used in the method of the invention.

6 Claims, 3 Drawing Sheets a. NaOH, H₂O; b. DIMETHYLDIOXIRANE (DMD); c. VINYL MAGNESIUM BROMIDE (2.2 EQUIV.); d. METHYLAMINE, TOLUENE; e. DIMETHYLAMINE, TOLUENE.

ANTI-ANGIOGENIC AGENTS

BACKGROUND OF THE INVENTION

Angiogenesis, the process of vascularization, has been implicated in a host of biological disorders including cancer, macular degeneration and arthritis. Spawned by the therapeutic potential associated with the inhibition of pathological angiogenesis, a flurry of activity has led to the discovery of a variety of antiangiogenic compounds which exhibit clinical utility. The discovery of 2-methoxyestradiol by Folkman et al has demonstrated evidence for potent antiangiogenic activity by the estrane steroid family and has provided the most potent endogenous mammalian inhibitor of tubulin polymerization yet discovered. (See U.S. Pat. No. 5,504,074.) Additionally, Fotsis et al have shown that of 2-methoxyestradiol exhibits in vitro anti-mitotic properties and reversible inhibition of cell proliferation while confluent cultures are unaffected. (See Fotsis, et. al. Nature 1994, 368, 237.) Preclinical and clinical trials have also shown 2-methoxyestradiol to be promising in the treatment of several angiogenic disorders.

2-Methoxyestradiol has been reported to exhibit antiangiogenic activity through the inhibition of tubulin polymerization by binding at the colchicine binding site. In contrast to 2-methoxyestradiol, colchicine exhibits minimal selectivity, is highly cytotoxic and as a result, its clinical use has been limited due to this low therapeutic index. Since the discovery of 2-methoxyestradiol, structure-activity relationship studies have yielded several 2-substituted estradiol derivatives that exhibit greater affinity for the colchicine binding site, as well as displaying greater cytotoxic responses in cancer cell lines. While the full clinical potential of 2-methoxyestradiol and these related compounds continues to be investigated, little remains known about the relationship between the observed antiangiogenic activity of 2-methoxyestradiol and its ability to bind to tubulin.

SUMMARY OF THE INVENTION

We have discovered that certain compounds within the scope of the general formulae set forth below in the claims are useful for treating mammalian diseases characterized by undesired cell mitosis. Without wishing to bind ourselves to any particular theory, such compounds generally inhibit microtubulic formation and tubulin polymerization and/or depolymerization. Compounds within the general formulae having said inhibiting activity are preferred. Preferred compositions may also exhibit a change (increase or decrease) in estrogen receptor binding, improved absorption, transport (e.g. through blood-brain barrier and cellular membranes), biological stability, or decreased toxicity. We have also discovered certain compounds useful in the method, as described by the general formulae of the claims.

A mammalian disease characterized by undesirable cell mitosis, as defined herein, includes but is not limited to excessive or abnormal stimulation of endothelia cells (e.g. atherosclerosis) solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, psoriasis, diabetic retinopathy and other ocular angiogenic diseases such as retinopathy of prematurity (retrolental fibroplastic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

Other features and advantages of the invention will be apparent from the following description of preferred embodiments thereof.

DETAILED DESCRIPTION OF THE PREFERRED EMBODIMENT OF THE INVENTION

Figure 1:
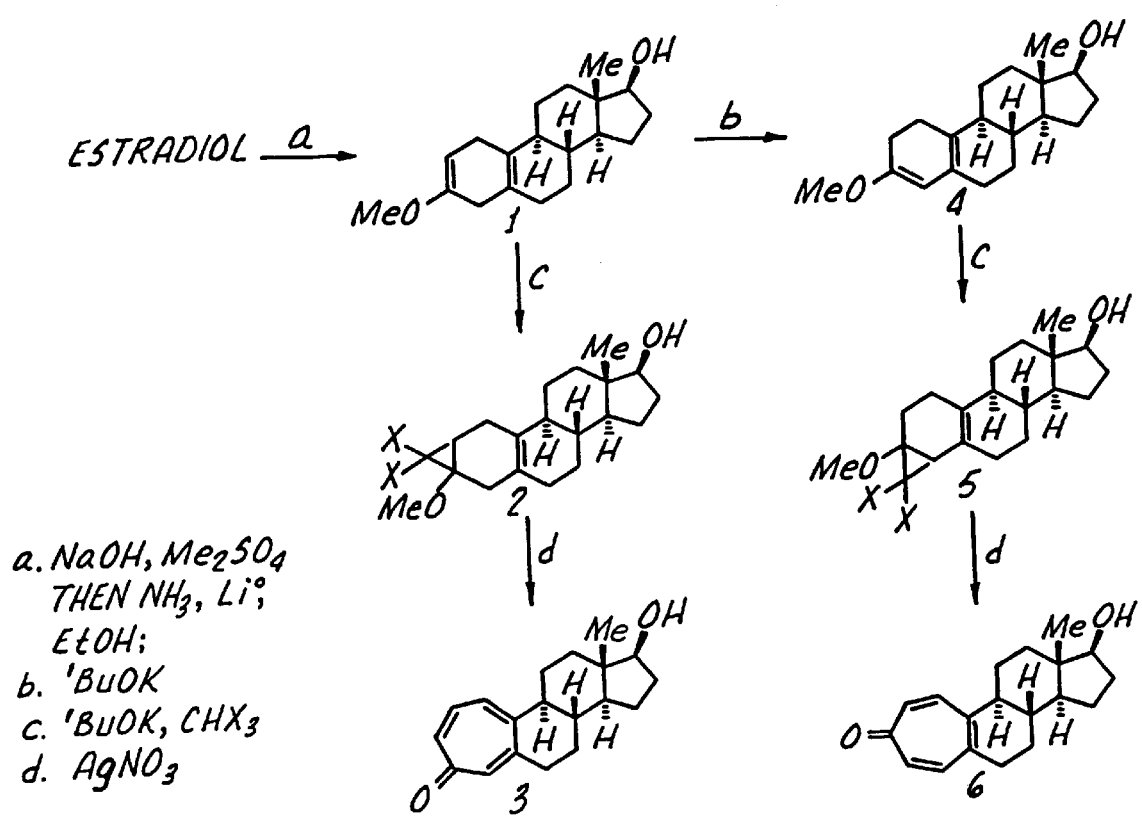
FIG. 1 is a reaction scheme outlining the synthesis of various homoestratrien-17β-olones of the invention.

As described below, compounds that are useful in accordance with the invention include novel derivatives that bind tubulin, inhibit microtubule formation or exhibit anti mitotic properties. Specific compounds according to the invention are described below.

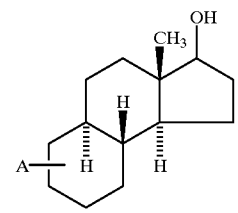

wherein A is a fused tropone having a general formula:

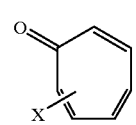

I

or

II

III

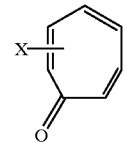

wherein X is selected from the group consisting of hydrogen, hydroxy, carboxy, halogen, nitro, $C_1$ to $C_{12}$ alkenyl, $C_1$ to $C_{12}$ alkyl, $C_1$ to $C_{12}$ alkoxy, SR, $NR_2$, $OSO_3^-$, $OSO_2NR_2$, $HNSO_3^-$, $NHSO_2NR_2$, $SSO_3^-$, $SSO_2 NR_2$, etc. wherein R is hydrogen or a $C_1$ to $C_6$ alkyl. Generally, R is selected to be adjacent to the carbonyl moiety of the tropone.

Preferably, X is selected from the group consisting of hydrogen, chloro, bromo, methoxy and ethoxy.

Most preferably, in the compounds of the invention A is a fused tropane having the general formula:

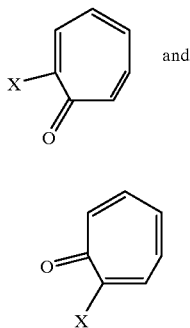

wherein X is as described above.

Anti-Mitotic Activity in Vitro

Anti-mitotic activity can be evaluated by testing the ability of a compound of the invention to inhibit tubulin polymerization and microtubule assembly in vitro. The tubulin/microtubule system is instrumental in the formation in the mitotic spindle, making it a prime target for anti-mitotic agents. In vitro tubulin polymerization assays are performed to serve as an estimate of the in vivo cytotoxic activity of designated compounds. Purified bovine brain tubulin (120 μl, 4 mg/ml), 240 μl PME (100 mm piperazine-n, n-bis(2-ethane-sulfonic acid i.e., pipes, ph 6.9, 1 mm MgSO$_4$, 2 mm ethyleneglycol-bis-(β-aminoethyl ether) N, N, N', N'-tetraacetic acid i.e. EGTA and 40 μl dimethyl sulfoxide i.e. DMSO, are combined and transferred to a 1 ml quartz cuvet. Polymerization is initiated by the addition of guanosine triphosphate i.e. GTP, (8 μl, 50 mM) and monitored turbidometrically in a Varian DMS 90 UV-Vis spectrophotometer in a temperature controlled cuvet holder at 30_C. Tubidity increases with increasing tubulin polymerization, giving a false absorbence reading and, over time, a polymerization curve. For these experiments, polymerization was monitored for 15 minutes, by which time a plateau was reached. 200 μM solutions (in DMSO) of compounds to be assayed were prepared, and substituted for portions of the DMSO in the polymerization mixture. For active compounds, increasing concentrations produce a proportional decrease in measured tubulin polymerization.

Indications

The invention can be used to treat any disease characterized by abnormal cell mitosis. Such diseases include, but are not limited to: abnormal stimulation of endothelial cells (e.g. atherosclerosis) solid tumors and tumor metastasis, benign tumors, for example, hemangiomas, acoustic neuromas, neurofibromas, trachomas and pyogenic granulomas, vascular malfunctions, abnormal wound healing, inflammatory and immune disorders. Bechet's disease, gout or gouty arthritis, abnormal angiogenesis accompanying rheumatoid arthritis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Synthesis of the Compounds of the Invention

Known compounds that are used in accordance with the invention and precursors to novel compounds according to the invention can be purchased, e.g., from Sigman Chemical Co., St. Louis, Steroids and Research Plus. Other compounds according to the invention can be synthesized according to known methods from publicly available precursors. Finally, many of the compounds of the invention may be synthesized according to the procedures of the Examples and/or the Figures or analogous procedures.

Administration

The compounds of the invention can be provided as physiologically acceptable formulations or compositions using known techniques, and these formulations can be administered by standard routes. In general, the formulations or compositions of the present invention may be administered by the topical, oral, rectal or parenteral (e.g. intravenous, subcutaneous or intramuscular) route. In addition, the compositions may be incorporated into biodegradable polymers allowing for sustained release, the polymers being implanted in the vicinity of where delivery is desired, for example, at the site of the tumor. The biodegradable polymers and their use are described in detail in Brem et al., J. Neurosurg. 74:441–446 (1991).

The dosage of the composition will depend on the condition being treated, the particular compound used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient, i.e. the compound of the invention, and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion or as a bolus, etc.

A tablet may be made by compression or molding, optionally with one or more accessory ingredients. Compressed tablets may be prepared by compressing, in a suitable machine, the active ingredients in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth, include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the active ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the active ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents conventional in the art having regard to the type of formulation in question, for example, those suitable for oral administration may include flavoring agents.

The invention is further illustrated by the following examples which are illustrative of specific modes of practicing the invention and are not intended as limiting the scope of the appended claims.

All reactions were carried out under argon with magnetic stirring unless otherwise noted. All solvents were distilled from appropriate desiccant under nitrogen immediately prior to use in reactions unless otherwise noted. All nuclear magnetic resonance spectra were obtained with a General Electric QE300 spectrometer and chemical shifts are reported in ppm. Elemental analyses were performed on a Perkin-Elmer PE2400 C, H and N analyzer. Analytical thin layer chromatography was performed on Merck silica gel 60 F-254 precoated plates (aluminum) and visualizations were effected with phosphomolybdic acid in ethanol. Radial chromatography was executed on a Chromatotron 7924 Harrison Research system. Column chromatography was performed on E. Merck silica 60 (230–400 mesh).

EXAMPLE 1

3-Methoxyestra-2,5(10)-dien-17β-ol (1)

To a solution of estradiol (10.0 g, 36.7 mmol) in ethanol (100 ml) at reflux was added NaOH (100 mmol) in water (10 ml) followed by the dropwise addition of methylsulfate ($Me_2SO_4$) (100 mmol). Neutralization with 10% HCl, subsequent concentration of the mixture followed by filtration through silica gel with ethyl ether, afforded 3-methoxyestradiol as white needles. Dissolving metal reduction of 3-methoxyestradiol was carried out via the methods described by Wilds and affording the known dihydroestradiene derivative as a white solid. (See Feiser, L. F., Feiser, M. "Reagents for Organic Synthesis", John Wiley and Sons, Inc., New York, 1967, pp. v, 583–4, 622–3.)

EXAMPLE 2

Mono-dibromocarbene adduct of β-Methoxyestra-2, 5(10)-dien-17β-ol (2)

3-Methoxyestra-2,5(10)-dien-17β-ol 1 (1.0 g, 3.5 mmol) and potassium tertiary-butoxide (t-BuOK) (10.4 mmol) were suspended in anhydrous ethyl ether (30 ml) at −30° C. followed by the dropwise addition of bromoform (1.3 ml) in ethyl ether (30 ml) over 1 hour. After stirring an additional 2 hours, the mixture was filtered through silica gel with ethyl ether and the filtrate concentrated. Flash chromatography of the residue yielded mono-adduct 2 as an equimolar mixture (0.82 g, 51%). $^1H$ NMR ($CDCl_3$) δ3.61 (t, J=8.1 Hz, 1H), 3.464/3.460 (s, 3H), 2.7–2.15 (m, 4H), 2.1–0.95 (complex, 17H), 0.704/0.688 (s, 3H). $^{13}C$ NMR ($CDCl_3$) δ126.68, 126.28, 124.72, 124.58, 82.18, 81.89, 64.57, 64.11, 54.73, 54.67, 51.65, 51.09, 50.36, 50.26, 46.18, 45.77, 43.78, 43.71, 39.69, 39.47, 37.55, 37.45, 34.78, 34.36, 32.10, 31.84, 31.58, 31.32, 30.99, 30.91, 27.10, 27.04, 26.31, 25.87, 25.73, 25.61, 23.49, 23.49.

EXAMPLE 3

A-Homo-1(10), 2,4a-estratrien-17β-ol-4-one (3)

Mono-adduct 2 (240 mg, 0.52 mmol) was dissolved in acetone (2 ml) and water (20 ml) was added, followed by the addition of silver nitrate (3.0 mmol). Reflux was initiated for 1 hour and after cooling, the mixture was concentrated, diluted with ethyl acetate, chromatographically filtered and concentrated. Radial chromatography of the residue yielded 3 as a white solid (140 mg, 91%). $^1H$ NMR ($CDCl_3$) δ7.095 (dd, J=9.24, 8.86 Hz, 2H), 7.004 (s, 1H), 6.896 (t, J=8.84 Hz, 1H), 3.723 (t, J=8.09 Hz, 1H), 2.808–2.695 (m, 1H), 2.510 (ddd, J=15.02, 3.08, 3.08, 1H), 2.23–1.17 (complex, 14H), 0.761 (s, 3H). $^{13}C$ NMR ($CDCl_3$) δ187.89, 153.00, 151.25, 140.26, 139.58, 136.39, 128.00, 81.83, 52.40, 44.88, 43.74, 36.57, 36.00, 33.63, 30.93, 25.57, 25.37, 23.82, 11.50.

EXAMPLE 4

3-Methoxyestra-3,5(10)-dien-17β-ol (4)

3-Methoxyestra-2,5(10)-dien-17β-ol 1 (2.0 g, 6.9 mmol) was added to a solution consisting of tetrahydofuran (15 ml), DMSO (5 ml) and t-BuOK (20.7 mmol). The resultant solution was stirred at ambient temperature for 10 hours at which time the solution was concentrated to Å5 ml and chromatographically filtered with 50% ethylether/petroleum ether (light) through 10 g of silica gel. The subsequent dimethyl sulfoxide (DMSO) free -powder was flash chromatographed affording 4 as white needles (1.30 g, 65% conversion, 91% based on recovered 1), Alternatively, crystallization by selective seeding (ether/methanol) was utilized, thereby circumventing chromatographic purification. $^1H$ NMR ($d^6$-acetone) δ4.629 (s, 1H), 3.505 (t, J=8.09 Hz, 1H), 3.431 (s, 3H), 2.15–0.98 (complex, 20H), 0.644 (s, 3H). $^{13}C$ NMR ($CDCl_3$) δ156.71, 126.56, 123.88, 96.55, 81.31, 54.19, 50.18, 46.03, 39.91, 37.54, 30.64, 30.58, 30.21, 27.71, 27.17, 25.67, 25.24, 23.22, 11.37.

EXAMPLE 5

Mono-dibromocarbene adduct of 3-Methoxyestra-3, 5(10)-dien-17β-ol (5)

3-Methoxyestra-3,5(10)-dien-17β-ol 4 (2.6 g, 9.0 mmol) and t-BuOK (27 mmol) were suspended in anhydrous ethyl ether (30 ml) at −40° C. followed by the dropwise addition of bromoform (5.2 ml) via syringe over 1 hour. After stirring an additional 3 hours, the mixture was filtered through silica gel with ethyl ether and the filtrate concentrated. Flash chromatography of the yielded mono-adduct 5 as an equimolar mixture (2.65 g, 64%). $^1$H NMR (CDCl$_3$) δ3.61 (t, J=8.08 Hz, 1H), 3.488/3.482 (s, 3H), 2.8–1.05 (complex, 21H), 0.761/0.748 (s, 3H).

EXAMPLE 6

A-Homo-1,4,5(10)-estratrien-17β-ol-3-one (6)

The mono-adduct 5 (100 mg, 0.22 mmol) was dissolved in acetone (1 ml) and water (10 ml) was added, followed by the addition of silver nitrate (1.0 mmol). Reflux was initiated for 0.5 hour and after cooling, the mixture was concentrated, diluted with ethyl acetate, filtered through silica gel and the filtrate concentrated. Flash chromatography of the resultant residue yielded 6 as a white solid (51 mg, 82%). $^1$H NMR (CDCl$_3$) δ7.268 (d, J=13.09 Hz, 1H), 6.921 (d, J=12.70 Hz, 1H), 6.882 (d, J=13.09 Hz, 1H), 6.874 (d, J=12.71 Hz, 1H), 3.728 (t, J=8.08 Hz, 1H), 2.90–2.53 (m, 2H), 2.28–1.18 (complex, 14H), 0.785 (s, 3H).

Figure 2:
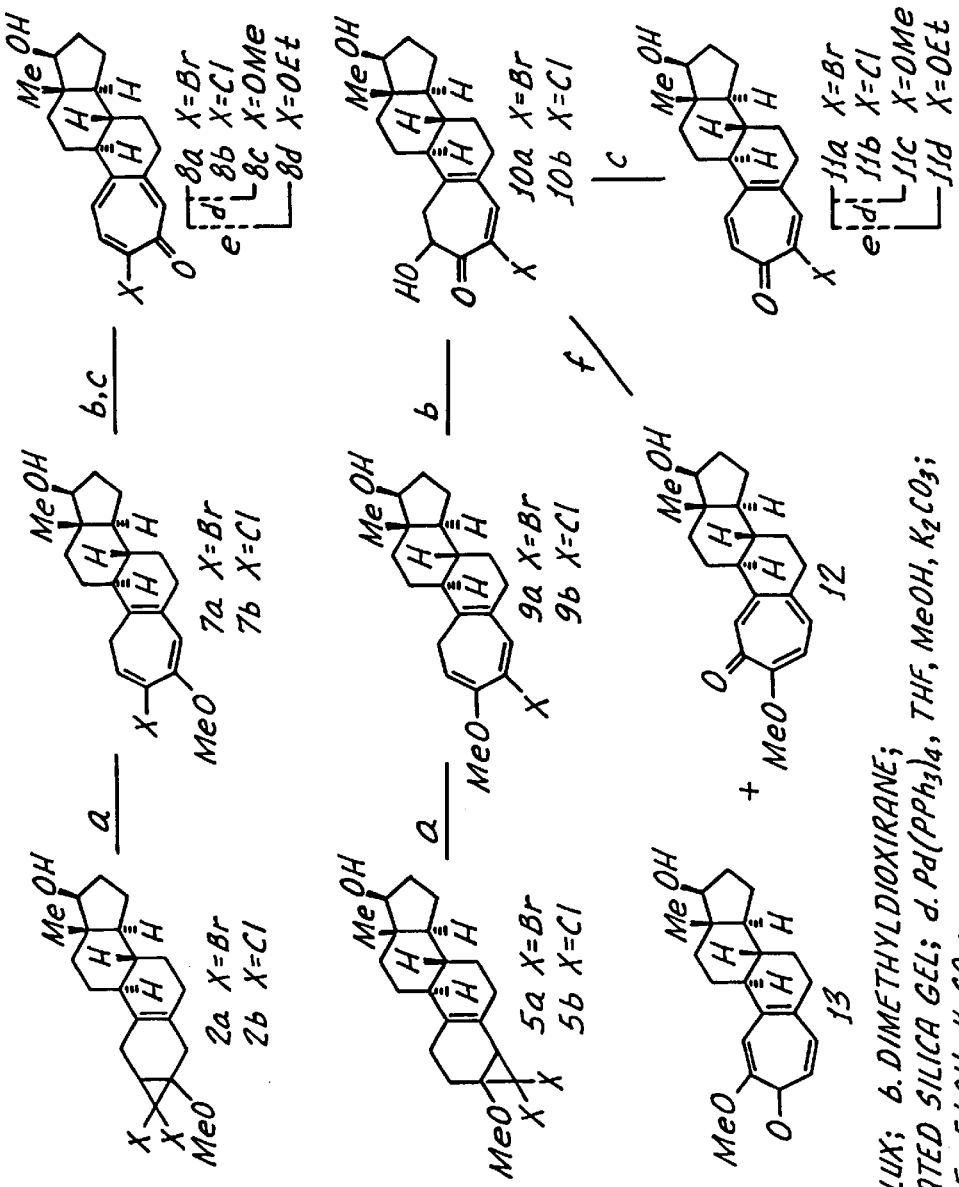
FIG. 2 is a reaction scheme outlining the synthesis of various halo and/or alkoxy-substituted homoestratrien (diene)ols and olones of the invention.
Figure 3:
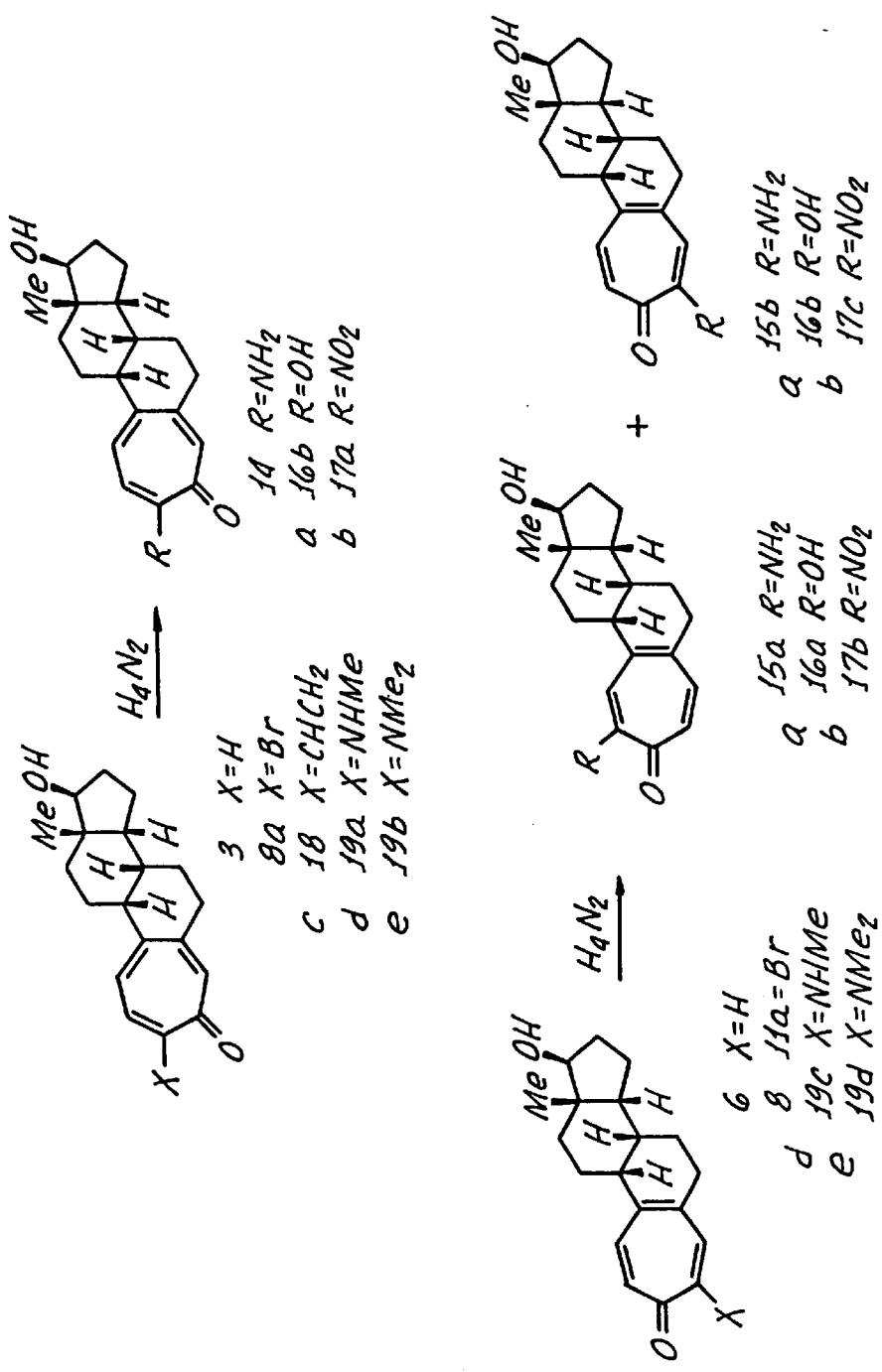
FIG. 3 is a reaction scheme outlining the synthesis of various alkenyl, amino, alkylamino, dialkyl amino, hydroxy and nitro-substituted olones of the invention.

The following general procedures were used to prepare the compounds of Examples 7 through 11. The general reaction scheme for these examples is outlined in FIG. 2.

General procedure (A): pyridine-induced ring expansion. The requisite mono-dihalocarbene adduct (1 g) was dissolved in pyridine (10 ml) and reflux was initiated for 5 hours. After cooling, the mixture was filtered through silica gel with ethyl ether and the filtrate concentrated under reduced pressure. The resultant gum was taken up in dichloromethane and flash chromatographed to afford the corresponding triene.

General procedure (B): epoxidation with dimethyldioxirane. The requisite halo-methoxytriene (0.25 g) was dissolved in 80% aqueous acetone (20 ml) and cooled to 0° C. in an open vessel. After portion-wise addition of a freshly prepared solution of dimethyldioxirane in acetone (0.1 M, 2.2 eq.), the mixture was allowed to warm to room temperature and monitored by TLC. (Dimethyldioxirane was prepared according to Adam et al, J. Org. Chem. 1987, 52, 2800.) Upon completion, solvents were removed under reduced pressure. Flash chromatography (SiO$_2$ acid impregnated with acidic bromoform) of the residue provided the requisite halo-tropone.

General procedure (C): Pd(PPh$_3$)$_4$-mediated alkoxylation. The requisite halo-tropone (10 mg) was dissolved in THF/alcohol (1:1, 5 ml) and Pd(P(C$_6$H$_5$)$_3$)$_4$ [or Pd(PPh$_3$)$_4$] (2 eg.) was added under argon (g). Initiation of reflux was followed by the addition of K$_2$CO$_3$ (2 eq.) in four equal portions over 1 hour. After an additional hour at reflux, the mixture was diluted with 30% methanolic chloroform, filtered through silica gel and the filtrate concentrated under reduced pressure. Radial chromatography of the residue afforded the corresponding α-alkoxy tropone.

General procedure (D): hydrazine mediated oxidative amination of tropones. The requisite tropone adduct (10 mg) was dissolved in TBF (1 mL) and hydrazine mono hydrate (1 mL) was added and the solution was stirred vigorously at room temperature for 48 hours. The mixture was then diluted with ethyl ether and filtered through silica gel eluting with ethyl ether. The filtrate was concentrated under reduced pressure and the oil was taken up in a minimum amount of dichloromethane and flash chromatographed (SiO$_2$) eluting with ethyl ether to afford the corresponding arninotropone as a yellow solid.

General procedure (E): conversion of aminotropones to nitrotropones. The requisite amino adduct (10 mg) was dissolved in acetone (degassed, 2.4 mL) under argon in an opaque flask. To this was added dimethyldioxirane (0.1 M, 2.4 mL, 7 equiv.) at room temperature. After 3 h the mixture was concentrated and flash chromatography (silica gel eluting with Et$_2$O) afforded the corresponding nitrotropone.

General procedure (F): conversion of halotropones to amino-tropones. The requisite halotropone adduct (100 mg) was dissolved in THF (1 mL) and the requisite amine (1 mL) was added at 0° C., the reaction was allowed to warm to room temperature and was followed by TLC. Upon completion (c.a. 5 hours), the mixture was concentrated, diluted with dichloromethane and filtered through silica gel with ethyl ether. The filtrate was concentrated under reduced pressure and the resultant gum was taken up in dichloromethane and flash chromatographed (SiO$_2$) eluting with ethyl ether to afford the corresponding aminotropone as a yellow solid.

EXAMPLE 7

3-Bromo-4-methoxy-A-Homo-2,4,5(10)-estratrien-17β-ol (7a) and 3-Chloro-4-methoxy-A-Homo-2,4,5 (10)-estratrien-17β-ol (7b)

The title compounds 7a and 7b were prepared from 2, respectively, as described in general procedure A (65% and 67% yield, respectively). $^1$H NMR 7a (CDCl$_3$) δ5.84 (t, J=8.09 Hz, 1H), 5.78 (s, 1H), 3.65 (t, J=8.1 Hz, 1H), 3.56 (s, 3H), 2.65 (δ, J=12.7 Hz, 1H), 2.62 (d, J=12.3 Hz, 1H), 2.2–0.95 (complex, 16H), 0.631 (s, 3H). $^{13}$C NMR (CDCl$_3$) δ153.97, 129.95, 128.75, 126.27, 114.43, 110.64, 81.21, 55.46, 49.95, 47.42, 44.04, 40.26, 37.77, 31.11, 30.78, 30.71, 28.80, 27.06, 23.27, 11.59.

EXAMPLE 8

3-Bromo-A-Homo-1(10), 2,4a-estratrien-17β-ol-4-one (8a) and 3-Chloro -A-Homo-1(10), 2,4a-estratrien-17β ol-4-one (8b)

The title compounds 8a and 8b were prepared from 7a and 7b respectively as described in general procedure B (53% and 46% yield, respectively). $^1$H NMR 8a (CDCl$_3$) δ7.98 (d, J=10.01 Hz, 1H), 7.149 (s, 1H), 6.72 (d, J=10.01 Hz, 1H), 3.69 (t, J=8.08 Hz, 1H), 2.77 (dt, J=15 Hz, J=8.2 Hz, 1H), 2.55 (dd, J=15 Hz, J=5.0 Hz, 1H), 2.25–1.95 (m, 4H), 1.9–1.25 (complex, 10H), 0.754 (s, 3H). $^{13}$C NMR 8a (CDCl$_3$) δ180.39, 152.90, 150.49, 139.78, 139.15, 136.36, 125.79, 81.82, 77.98, 77.56, 77.14, 52.30, 44.92, 43.68, 36.50, 36.05, 33.54, 30.93, 25.54, 25.38, 23.79, 11.48.

EXAMPLE 9

3-Methoxy-A-Homo-1(10), 2,4a-estratrien-17β-ol-4-one (8c) and 3-Ethoxy-A-Homo-1(10), 2,4a-estratrien-17β-ol-4-one (8d)

The title compounds 8c and 8d were prepared from 8a as described in general procedure C (77% and 82% yield, respectively). $^1$H NMR 8c (CDCl$_3$) δ7.233 (s, 1H), 6.99 (d, J=10.8 Hz, 1H), 6.69 (d, J=10.4 Hz, 1H), 3.91 (s, 3H), 3.73 (t, J=8.47 Hz, 1H), 2.83 (m, 1H), 2.61 (m, 1H), 2.3–1.2 (complex, 14H), 0.768 (s, 3H).

EXAMPLE 10

4-Bromo-3-methoxy-A-Homo-2,4,5(10)-estratrien-17β-ol (9a) and 4-Chloro-3-methoxy-A-Homo-2,4,5 (10)-estratrien-17β-ol (9b)

Title compounds 9a and 9b were prepared as described in general procedure A (68% and 60% yield, respectively) from (5). $^1$H NMR 9a (CDCl$_3$) δ6.89 (s, 1H), 4.70 (t, J=8.1 Hz, 1H), 3.57 (t, J=8.1 Hz, 1H), 3.56 (s, 3H), 2.5–1.0 (complex, 18H), 0.861 (s, 3H).

EXAMPLE 11

4-Bromo-A-Homo-4,5(10)-estradien-2,17β-diol-3-one 11a and 4 Chloro-A-Homo-4,5(10)-estradien-2, 17β-diol-3-one 10b The title compounds 11a and 11b were prepared from 9a as described in general procedure B. (62% and 45% yield, respectively). $^1$H NMR 11a (CDCl$_3$) δ7.35 (s, 1H), 4.02 (d, J=13.9 Hz, 1H), 3.71 (t, J=8.08 Hz, 1H), 2.65 (d, J=15 Hz, 1H), 2.43 (t, J=14 Hz, 1H), 2.3–1.05 (complex, 17H), 0.807 (s, 3H). $^{13}$C NMR 11a (CDCl$_3$) δ195.0, 149.4, 147.8, 131.9, 120.7, 82.1, 77.7, 74.5, 50.2, 48.3, 43.9, 39.3, 37.6, 32.6, 31.2, 27.3, 26.8, 23.4, 11.8.

EXAMPLE 12

4-Methoxy-A-Homo-1,4,5(10)-estratrien-17β-ol-3-one (11c) and 3-Ethoxy-A-Homo-1,4,5(10)-estratrien-17β-ol-3-one (11d)

The title compounds 11c and 11d were prepared from (11a) as described in general procedure C. (77% and 71% yield, respectively). $^1$H NMR 8c (CDCl$_3$) δ7.233 (s, 1H), 6.99 (δ, J=10.8 Hz, 1H), 6.69 (d, i=10.4 Hz, 1H), 3.91 (s, 3H), 3.73 (t, J=8.47 Hz, 1H), 2.83 (m, 1H), 2.61 (m, 1H), 2.3–1.2 (complex, 14H), 0.768 (s, 3H).

EXAMPLE 13

3-Methoxy-A-Homo-1(10), 3,4a-estratrien-17β-ol-2-one (12) and 2-Methoxy-A-Homo-1,4,5(10)-estratrien-17β-ol-3-one (13)

Hydroxydienone 10a (20 mg, 0.05 mmol) was dissolved in acetone (1 ml) and water (10 ml) was added, followed by the addition of silver nitrate (0.025 mmol). Reflux was initiated for 5 hours and after cooling, the mixture was concentrated, diluted with 30% methanol (MeOH) in CHCl$_3$, chromatographically filtered and concentrated to 5 ml. The resultant mixture was treated with TMSCHN$_2$ (0.25 mmol, 2M in hexane) concentrated. Flash chromatography of the residue yielded 12 and 13 as a white solids (42% and 44% yield respectively). $^1$H NMR 12 (CDCl$_3$) δ7.05 (m, 2H), 6.95 (s, 1H), 3.92 (s, 3H), 3.76 (t, J=8.8 Hz, 1H), 2.90–2.65 (m, 2H), 2.33–2.1 (m, 2H), 2.01 (dt, J=12.3 Hz, J=3.5 Hz, 1H), 1.98–1.81 (m, 1H), 1.75–1.2 (complex, 10H), 0.812 (s, 3H). $^1$H NMR 13 (CDCl$_3$) δ7.32 (s, 1H), 6.88 (d, J=10.4 Hz, 1H), 6.60 (d, J=10.4 Hz, 1H), 3.91 (s, 3H), 3.73 (t, J=8.1 Hz, 1H), 2.90–2.5 (m, 2H), 2.3–1.95 (m, 4H), 1.8–1.2 (complex, 10H), 0.761 (s, 3H).

EXAMPLE 14

3-Amino-A-homo-1(10), 2,4a-estratrien-17β-ol-4-one (14)

The title compound 14 (yellow powder, R$_f$=0.11, 82%) was prepared from 3 as described in general procedure D. $^1$H NMR (14) (CDCl$_3$) δ7.25 (s, 1H), 7.11 (d, J=10 Hz, 1H), 6.78 (d, J=11 Hz, 1H), 5.67 (broad s, 2H), 3.74 (t, J=8.09 Hz, 1H), 2.9–2.62 (m, 2H), 2.2–2.1 (complex m, 2), 1.98 (dt, J=13.1 Hz, J=3.5 Hz, 1H), 1.8–1.15 (complex, 11H), 0.776 (s, 3H).

EXAMPLE 15

2-Amino-A-homo-1,4,5(10)-estratrien-17β-ol-3-one 15a and 4-Amino-A-homo-1, 4,5(10)-estratrien-17β-ol-3-one (15b)

The title compounds 15a (yellow oil, R$_f$=0.054, 40%) and 15b (yellow oil, R$_f$=0.108, 41%) were prepared from 6 as described in general procedure D. $^1$H NMR (15a) (CDCl$_3$) δ7.28 (d, J=10.8 Hz, 1H), 7.12 (s, 1H), 7.06 (d, J=10.2 Hz, 1H), 5.6 (broad s, 2H), 3.74 (dd, J=8.5 Hz, J=8.1 Hz, 1H), 2.76 (dt, J=8.5 Hz, J=6 Hz, 1H), 2.34–1.95 (m, 3H), 1.98 (dt, J=13.1 Hz, J=3.5 Hz, 1H), 1.85–1.10 (complex, 11H), 0.802 (s, 3H). $^1$H NMR (15b)(CDCl$_3$) δ7.40 (d, J=12.3 Hz, 1H), 7.06 (d, J=12.7 Hz, 1H), 6.75 (s, 1H), 5.55 (broad s, 2H), 3.73 (t, J=8.5 Hz, J=8.1 Hz, 1H), 2.9–2.7 (m, 1H), 2.30–2.1 (m, 3H), 1.97 (dt, J=12.7 Hz, J=3.5 Hz, 1H), 1.9–1.2 (complex, 11H), 0.790 (s, 3H).

EXAMPLE 16

A-homo-1,4,5(10)-estratrien-2, 17β-diol-3-one 16a and A-homo-1(10), 2,4a -estratrien-3,17β-diol-3-one (16a)

The title compounds 16a (brown residue, R$_f$=0.2 elongated, 36%) and 16b (brown oil, R$_f$=0.19 elongated, 42%) were prepared from 15a and 14, respectively, by treatment of the requisite aminotropone (10 mg) in MeOH (12 mL) with KOH (3.8 mL, 2N) held at reflux for 2 days. The resultant dark mixture was diluted with water (19 mL) and washed with CH$_2$Cl$_2$ (5 mL). The aqueous layer was then acidified with 1N HCl, extracted with CH$_2$Cl$_2$ (45 mL), dried over Na$_2$SO$_4$, and then concentrated to afford the corresponding tropolones (positive Fe(III) test). $^1$H NMR 16b (CDCl$_3$) δ6.98 (broad s, 1H), 5.36–5.3 (complex, 2H), 5.1 (broad s, 1H), 3.73 (t, J=8.1 Hz, 0.5H), 3.64 (t, J=8.1 Hz, 0.5H), 2.8 (m, 1H), 2.53 (sextet, J=7.7 Hz, 2H), 2.35 (t, J=7.3 Hz, 2H), 2.1–1.1 (complex, 11H), 0.88 (s, 3H).

EXAMPLE 17

3-Nitro-A-homo-1(10), 2,4a-estratrien-17β-ol-4-one 17a, 2-Nitro-A-homo-1,4, 5(10)-estratrien-17β-ol-3-one 17b, and 4-Nitro-A-homo-1,4,5(10)-estratrien-17β-ol-3-one 17c The title compounds 17a (yellow residue, R$_f$=0.48, 72%), 17b (yellow residue, R$_f$=0.49, 52%), and 17c (yellow residue, R$_f$=0.52, 29%) were prepared from 14,15a, and 15b, respectively, as described in general procedure E. $^1$H NMR 17a (CDCl$_3$) δ7.86 (d, J=9 Hz, 1H), 7.83 (s, 1H), 7.47 (d, J=9 Hz, 1H), 3.753 (t, J=8.79 Hz, 1H), 2.98–2.93 (m, 2H), 2.4–1.2 (complex, 14H), 0.800 (s, 3H). $^1$H NMR (17b) (CDCl$_3$) δ8.18 (s, 1H), 7.96 (d, J=8.5 Hz, 1H), 7.21 (d, J=9 Hz, 1H), 3.76 (t, J=8.08 Hz, 1H), 3.0–2.90 (m, 2H), 3.05–3.0 (m, 3H), 2.90 (t, J=7.71 Hz, 1H), 2.7–1.05 (m, 10H), 0.89 (s, 3H). $^1$H NMR (17c) (CDCl$_3$) δ7.96 (d, J=11 Hz, 1H), 7.43 (d, J=10 Hz, 1H), 7.34 (s, 1H), 3.79 (t, J=8.5 Hz, 1H), 2.95–1.2 (complex, 16H), 0.799 (s, 3H).

EXAMPLE 18

3-Vinyl-A-homo-1(10), 2,4a-estratrien-17β-ol-4-one 18

The title compound 18 (oil, R$_f$=0.61 with ethyl ether, 61%) was prepared from 8a by dissolution of (10 mg) in THF (2 mL) followed by the addition of vinylmagnesium bromide dropwise to the loss of starting material by TLC. The resultant mixture was then filtered through silica gel and, after concentration under reduced pressure, flash chromatographed (SiO$_2$ eluting with ethyl ether). $^1$H NMR 18 (CDCl$_3$) δ6.64 (d, J=12 Hz, 1H), 6.60 (d, J=12 Hz, 1H), 6.5 (dd, J=13 Hz, J =8 Hz, 1H), 6.05 (d, J=13 Hz, 1H), 5.8 (d, J=8 Hz, 1H), 5.75 (t, J=4 Hz, 1H), 3.71 (t, J=8.48 Hz, 1H), 2.5 (dt, J=19 Hz, J=5.8 Hz, 1H), 2.36 (d, J=7.7 Hz, 1H), 2.2–1.2 (complex, 14H), 0.79 (s, 3H). $^M/_z$[M-18]=292.

EXAMPLE 19

3-Methylamino-A-homo-1(10), 2,4a-estratrien-17β-ol-4-one (19a), 3-Dimethylamino-A-homo-1(10), 2, 4a-estratrien-17β-ol-4-one (19b), 4-Methylamino-A-homo-1,4,5(10)-estratrien-17β-ol-3-one (19c), and 4-Dimethylamino-A-homo-1,4,5(10)-estratrien-17β-ol-3-one (19d)

The title compounds were prepared from the corresponding bromotropones as described in general procedure F. 19a (yellow oil, R$_f$=0.11 with 30% acetone in chloroform, 74%); 19b (yellow oil, R$_f$=0.21 with 30% acetone in chloroform, 82%); 19c (yellow oil, R$_f$=0.13 with 30% acetone in chloroform, 62%); 19d (yellow oil, R$_f$=0.20 with 30% acetone in chloroform, 77%); $^1$H NMR 19a (CDCl$_3$) δ7.50 (s, 1H), 7.49 (d, J=9 Hz, 1H), 7.33 (d, J=9 Hz, 1H), 6.1 (broad s, 1H), 3.74 (t, J=8.09 Hz, 1H), 3.00 (d, J=5 Hz, 3H), 2.9–2.88 (m, 2H), 2.4–2.1 (complex m, 12H), 0.79 (s, 3H). $^1$H NMR 19c (CDCl$_3$) δ7.00 (d, J=12 Hz, 1H), 6.97 (s, 1H), 6.5 (d, J=12 Hz, 1H), 3.73 (t, J=8.08 Hz, 1H), 3.15–2.95 (m, 2H), 3.04 (s, 6H), 2.8–1.2 (m, 14H), 0.77 (s, 3H).

EXAMPLE 20

Table 1 illustrates the inhibitory effects on tubulin polymerization in vitro exhibited by compounds of this invention and colchicine. The method is given above in-vitro assay for anti-miotic activity.

TABLE 1

| COMPOUND | 1C$_{50}$ (μM) |
| --- | --- |
| colchicine | 11.2 |
| 3 | 7.2 |
| 6 | 4.4 |
| 8a | 2.9 |
| 8b | 2.8 |
| 8c | 8.1 |
| 11a | 11.2 |
| 11b | 9.8 |
| 11c | 2.1 |
| 11d | 5.9 |
| 12 | 27.5 |
| 13 | 29.8 |
| 14 | 14.4 |
| 15a | 16.5 |
| 15b | 9.2 |
| 16a | 14.9 |
| 16b | 22.8 |
| 17a | 52 |
| 18 | 14.2 |
| 19a | 60.7 |
| 19b | 14.3 |
| 19c | 19.4 |
| 19d | 46.8 |

While particular embodiments of the invention have been described, it will be understood of course that the invention is not limited thereto since many obvious modifications can be made and it is intended to include within this invention any such modifications as will fall within the scope of the appended claims.

For example, the compounds utilized in the method of the present invention may include certain 17-esters, wherein the hydrogen radical of the 17-hydroxy is replaced by C$_1$ to C$_{12}$ alkylcarbo, C$_6$ to C$_{10}$ arylcarbo or C$_5$ to C$_{10}$ heteroarylcarbo wherein said heteroatom may comprise sulfur, oxygen or nitrogen, as in, for example, furyl, thienyl or pyridyl. These 17-ester derivatives are prepared by esterifying the 17-hydroxyl with appropriate carboxylic acid by methods known in the art. In addition, the 17-hydroxy may be oxidized by methods known in the art to provide 17-keto derivatives which are also useful in the method of the present invention. Finally, the keto derivatives may be converted to various other derivatives by reaction with bisulfite, hydroxylamine, hydrazine, semicarbizide, alcohol, etc. to provide the corresponding bisulfite, oxime, hydrazone, semicarbazone, acetal, etc.

Having now described the invention, we claim:

1. A method for treating a mammalian disease characterized by undesirable angiogenesis, said method comprising administering to a mammal having said undesirable angiogenesis a compound of the formula below, said compound being administered in an amount sufficient to inhibit angiogenesis:

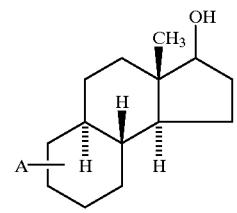

wherein A is a fused tropone having a general formula:

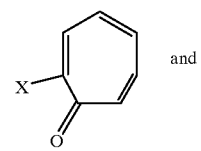

IV and

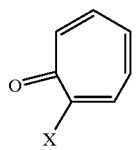

V wherein X is selected from the group consisting of H, Cl, Br, methoxy and ethoxy.

2. A compound for treating a mammalian disease characterized by undesirable angiogenesis, of the formula below:

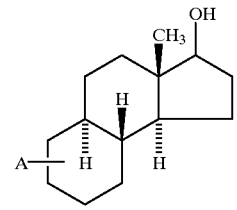

wherein A is a fused tropone having a general formula:

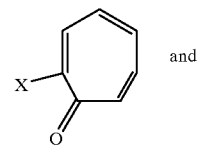

IV and

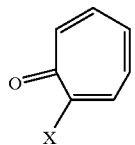

V wherein X is selected from the group consisting of H, Cl, Br, methoxy and ethoxy.

3. A method for treating a mammalian disease characterized by undesirable angiogenesis, said method comprising administering to a mammal having said undesirable angiogenesis, a compound of the formula below, said compound being administered in an amount sufficient to inhibit angiogenesis:

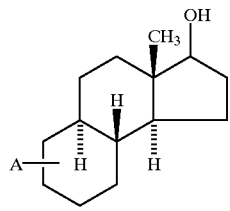

wherein A is

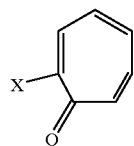

and X is selected from the group consisting of chloro and bromo.

4. A method for treating a mammalian disease characterized by undesirable angiogenesis, said method comprising administering to a mammal having said undesirable angiogenesis, a compound of the formula below, said compound being administered in an amount sufficient to inhibit angiogenesis:

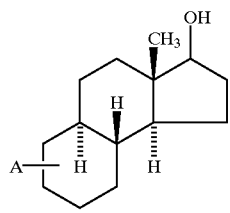

wherein A is

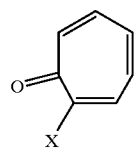

and X is methoxy.

5. A compound for treating a mammalian disease characterized by undesirable angiogenesis, of the formula below:

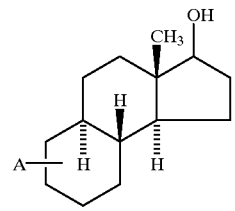

wherein A is

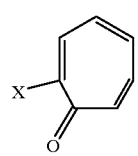

and X is selected from the group consisting of chloro and bromo.

6. A compound for treating a mammalian disease characterized by undesirable angiogenesis, of the formula below

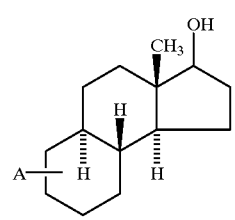

wherein A is

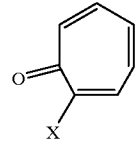

and X is methoxy.

* * * * *

UNITED STATES PATENT AND TRADEMARK OFFICE
CERTIFICATE OF CORRECTION

| | |
|---|---|
| PATENT NO. | : 6,271,220 B1 |
| DATED | : August 7, 2001 |
| INVENTOR(S) | : Garst et al. |

It is certified that error appears in the above-identified patent and that said Letters Patent is hereby corrected as shown below:

<u>Column 7,</u>
Line 61, delete "arninotropane" and insert in place thereof -- aminotropane --

<u>Column 9,</u>
Line 57, delete "(complex m, 2)" and insert in place thereof -- (complex m, 2H) --

Signed and Sealed this

Twelfth Day of March, 2002

*Attest:*

*Attesting Officer*

JAMES E. ROGAN
*Director of the United States Patent and Trademark Office*